United States Patent
Avila et al.

(10) Patent No.: US 8,010,184 B2
(45) Date of Patent: Aug. 30, 2011

(54) METHOD AND APPARATUS FOR AUTOMATICALLY CHARACTERIZING A MALIGNANCY

(75) Inventors: Ricardo Avila, Clifton Park, NY (US); Floribertus Heukensfeldt Jansen, Ballston Lake, NY (US); Dinko Gonzalez Trotter, Clifton Park, NY (US); James Miller, Clifton Park, NY (US); Ravindra Manjeshwar, Guilderland, NY (US); Thomas Sebastian, Flemington, NJ (US)

(73) Assignee: General Electric Company, Niskayuna, NY (US)

( * ) Notice: Subject to any disclaimer, the term of this patent is extended or adjusted under 35 U.S.C. 154(b) by 1672 days.

(21) Appl. No.: 11/291,830

(22) Filed: Nov. 30, 2005
(Under 37 CFR 1.47)

(65) Prior Publication Data
US 2007/0167697 A1 Jul. 19, 2007

(51) Int. Cl.
*A61B 5/055* (2006.01)
(52) U.S. Cl. ... 600/427; 600/431; 600/436; 250/363.03; 250/363.04
(58) Field of Classification Search ......... 600/407–436; 378/4; 250/363.02–363.04
See application file for complete search history.

(56) References Cited

U.S. PATENT DOCUMENTS

| 6,490,476 | B1 * | 12/2002 | Townsend et al. | 600/427 |
|---|---|---|---|---|
| 6,631,284 | B2 * | 10/2003 | Nutt et al. | 600/427 |
| 7,603,165 | B2 * | 10/2009 | Townsend et al. | 600/427 |
| 2003/0004405 | A1 * | 1/2003 | Townsend et al. | 600/407 |
| 2004/0030246 | A1 * | 2/2004 | Townsend et al. | 600/427 |
| 2007/0081712 | A1 * | 4/2007 | Huang et al. | 382/128 |
| 2010/0032575 | A1 * | 2/2010 | Iagaru et al. | 250/362 |

FOREIGN PATENT DOCUMENTS
WO WO2005001740 A2 1/2005
* cited by examiner

Primary Examiner — Sanjay Cattungal
(74) Attorney, Agent, or Firm — Scott J. Asmus

(57) ABSTRACT

A region of interest is automatically evaluated. The automatic evaluation is based on assessments of one or more characteristics. The one or more characteristics of the region of interest are assessed in a plurality of image data sets acquired by a respective plurality of imaging modalities. In some embodiments, the evaluation is based on assessments of one or more characteristics for each region of interest derived from a combination of structural and functional image data. In one embodiment, the set of structural image data is a set of CT image data and the set of functional image data is a set of PET image data. The one or more lesions may be detected in the structural and/or functional image data by automated routines or by a visual inspection by a clinician or other reviewer.

30 Claims, 3 Drawing Sheets

METHOD AND APPARATUS FOR AUTOMATICALLY CHARACTERIZING A MALIGNANCY

BACKGROUND OF THE INVENTION

The present invention relates generally to the field of medical imaging and more specifically to the evaluation of features of interest in image data acquired using different imaging modalities. In particular, the present invention relates to the evaluation of malignancies observable in computed tomography (CT) and positron emission tomography (PET) image data.

Non-invasive imaging broadly encompasses techniques for generating images of the internal structures or regions of a person that are otherwise inaccessible for visual inspection. One of the best known uses of non-invasive imaging is in the medical arts where these techniques are used to generate images of organs and/or bones inside a patient which would otherwise not be visible. One class of medical non-invasive imaging techniques is based on the generation of structural images of internal structures which depict the physical arrangement, composition, or properties of the imaged region. Example of such modalities include X-ray based techniques, such as CT and tomosynthesis. In these X-ray based techniques, the attenuation of X-rays by the patient is measured at different view angles and this information is used to reconstruct two-dimensional images and/or three-dimensional volumes of the imaged region.

Another modality used to generate structural images is magnetic resonance imaging (MRI). In MRI, the tissues undergoing imaging are subjected to strong magnetic fields and to radio wave perturbations which produce measurable signals as the tissues of the body align and realign themselves based upon their composition. These signals may then be used to reconstruct structural images that reflect the physical arrangement of tissues based on these different gyromagnetic responses. Another example of a structural imaging modality is ultrasound imaging, in which the differential reflection of acoustic waves by the internal structures of a patient is used to reconstruct images of the internal anatomy.

While structural imaging modalities generate images of the physical composition or arrangement of a region of interest, functional imaging modalities generate images reflecting the chemical composition or metabolic activity of the region of interest. Examples, of such functional imaging modalities include nuclear medicine, single-photon emission computed tomography (SPECT), and PET. These modalities typically detect photons or gamma rays, either directly or indirectly, which are generated by a radioactive tracer introduced into the patient. Based on the type of metaboland, sugar, or other compound into which the radioactive tracer is incorporated, the radioactive tracer is accumulated in different parts of the patient and measurement of the resulting gamma rays can be used to localize and image the accumulation of the tracer. For example, tumors may disproportionately utilize glucose or other substrates relative to other tissues such that the tumors may be detected and localized using radioactively tagged deoxyglucose. Other examples of functional imaging modalities include functional MRI, in which chemical composition information is obtained, and fluorescence imaging.

The different functionalities of structural and functional imaging may be combined to provide more information to a diagnostician than either modality alone. For example, in the case of combined PET/CT scanners, a clinician is able to acquire both PET and CT image data that can be used in conjunction to detect tumors or to evaluate the progression of a tumor. In such an example, the clinician typically evaluates different malignancy characteristics that can be measured in each type of image data. In particular, the PET image data provides useful metabolic information, such as the molecular signature of disease, while the CT image data provides useful anatomic and geometric information in the form of high-resolution images and volume renderings. The malignancy characteristics derived from each type of data may then be considered together and utilized to characterize suspicious areas as well as to accurately assess cancer stages.

While the availability and analysis of both functional and structural image data (such as PET and CT images) provides diagnostic opportunities, several challenges to such techniques still exist. For example, in the case of combined PET/CT systems the image data is typically visually inspected by a clinician who provides a subjective assessment based on the visual inspection. However, the presentation of subtle disease state presentations, in either PET or CT image data, may be problematic. For example, a clinician may not know how to quantitatively determine whether a slight increase in a PET signal is due to a benign process or to a malignant process. Proper interpretation of this data typically requires a thorough understanding of the physics processes and image formation techniques involved, which may not be information available to or known by the average practicing clinician. Furthermore, even if this information were known by the clinician, the calculations involved to quantify and assess the significance of a signal change would be too laborious to manually perform on a regular basis.

Furthermore, few clinicians have the knowledge or experience to fully understand and interpret the combined PET and CT data. Typically a clinician is primarily trained in the interpretation of image data from one type of image modality, but not both. Furthermore, synergies exist in the combined PET and CT image data such that the combined data may contain critical information that is not obvious or apparent in the uncombined image data. Apprehension of this synergistic information may not be possible by a clinician trained with respect to only one of the image modalities or inexperienced in the evaluation of such combined image data sets.

BRIEF DESCRIPTION OF THE INVENTION

In accordance with an exemplary embodiment of the present technique, a method is provided for evaluating a region of interest. The method includes the step of assessing one or more characteristics of a region of interest in a plurality of image data sets acquired by a respective plurality of imaging modalities. The region of interest is automatically evaluated based on the one or more characteristics. One or more machine-readable media are also provided that affords some or all of the functionality of the type defined by this method.

An analysis system is provided. The analysis system comprises analysis circuitry configured to assess one or more characteristics of a region of interest in a plurality of image data sets acquired by a respective plurality of imaging modalities. The analysis circuitry is also configured to evaluate the region of interest based on the one or more characteristics.

BRIEF DESCRIPTION OF THE DRAWINGS

The foregoing and other advantages and features of the invention will become apparent upon reading the following detailed description and upon reference to the drawings in which.

DETAILED DESCRIPTION OF SPECIFIC EMBODIMENTS

The present invention provides for the automatic or semi-automatic assessment of cancerous or potentially cancerous tissues using multiple sets of image data, such as a set of functional image data and a set of structural image data. The respective sets of image data may be concurrently acquired such as using a positron emission tomography/computed tomography (PET/CT) system, or may be acquired serially using combined or separate imaging systems. The automated analysis routines employed allow for a quantitative analysis of malignancy characteristics of identified regions of interest within the functional and/or structural image data sets. These regions of interest may be identified in an automatic fashion. In this manner accurate, quantifiable results may be obtained to assist a clinician in the evaluation of a patient.

Figure 1:
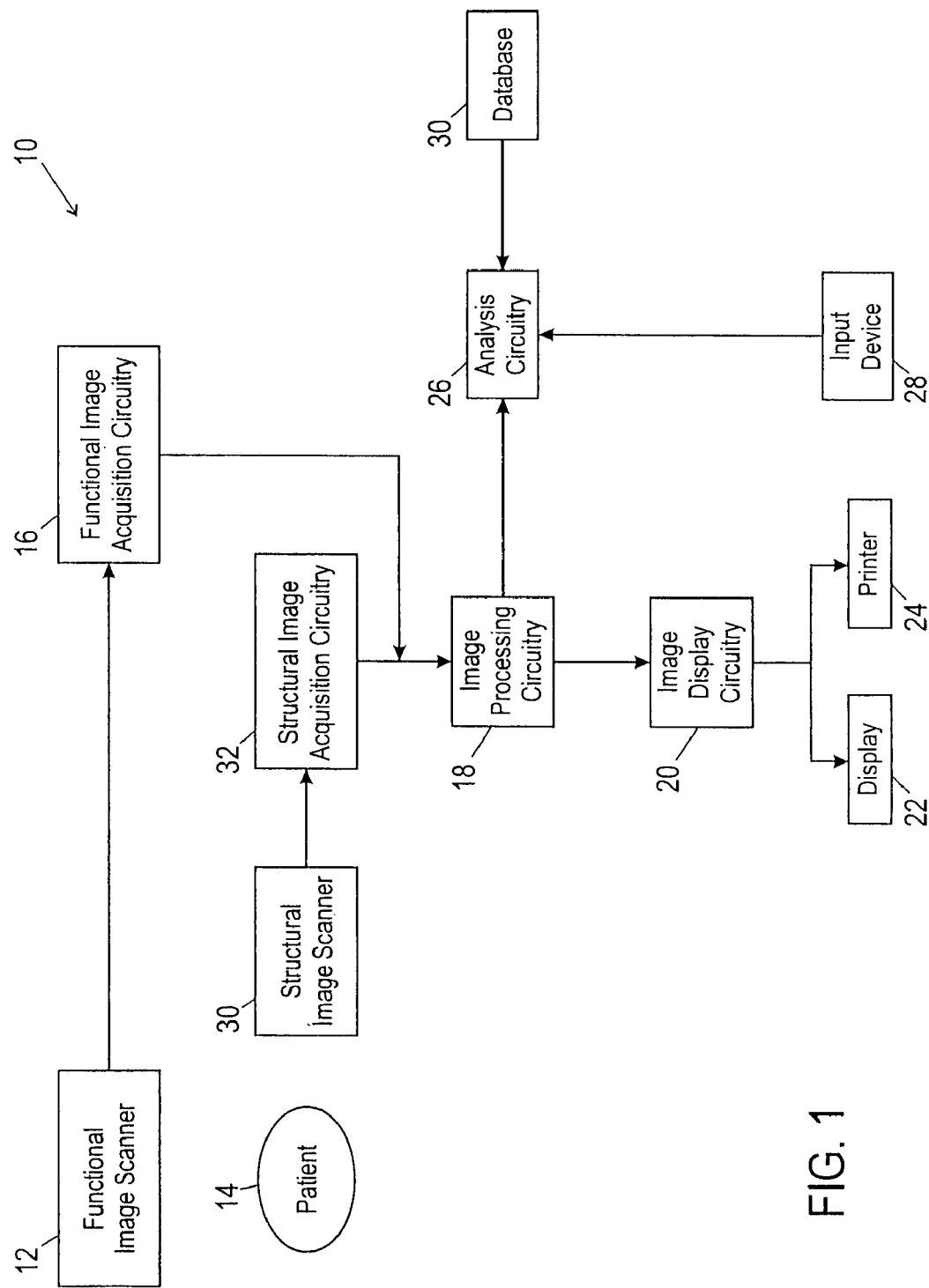
FIG. 1 is a diagrammatical view of an exemplary imaging system for use in accordance with the present technique.

In FIG. 1, an exemplary image analysis system 10 for use in accordance with the present technique is provided. For simplicity, the image analysis system 10 is depicted as comprising both functional and structural imaging modalities and combined image processing circuitry. However, as noted above, these imaging modalities and/or their associated image processing circuitry may be separate from one another with their respective image data being jointly provided for analysis as provided herein. Likewise, as noted above, more than one structural and/or functional imaging modality may be present. However, for simplicity and comprehensiveness, a single structural imaging modality and a single functional imaging modality are depicted in FIG. 1.

Returning to FIG. 1, the image analysis system 10 is depicted as including a functional image scanner 12 configured to acquire data for generating functional images of a patient 14. The functional image scanner 12 represents the data acquisition components of a functional imaging modality, such as a PET, nuclear medicine, single-photon emission computed tomography (SPECT), fluorescence imaging, or functional magnetic resonance imaging system. Likewise, functional image acquisition circuitry 16 is depicted. The acquisition circuitry 16 is configured to acquire signals from the functional image scanner 12 and to provide any conversion (such as analog to digital conversion) or processing (such as image normalization, gain correction, artifact correction, and so forth) typically performed to facilitate the generation of suitable functional images. In the depicted embodiment, image processing circuitry 18 receives the acquired signals from the functional image acquisition circuitry 16 and, via suitable reconstruction techniques, generates functional images and/or volumes from the acquired functional image data. The generated images or volumes may be provided to image display circuitry 20 configured to display the functional images or volumes in a suitable format, such as on a display 22 or as an image printed by printer 24.

In addition, the functional images and/or volumes generated by the image processing circuitry 18 are provided to analysis circuitry 26 in the depicted embodiment. The analysis circuitry 26 analyzes the functional images and/or volumes in accordance with analysis routines, such as computer executable routines that may be run on general purpose or dedicated circuitry. In addition to the functional images and/or volumes, the analysis circuitry may receive operator inputs via one or more input devices 28, such as a keyboard and/or mouse. These inputs may include configuration information or other inputs that may select the analysis routine to be executed or that may affect the operation of such an analysis routine, such as by specifying variables or factors taken into account by the analysis routines. Furthermore, inputs may be provided to the analysis circuitry 26 from a database 30 or other source of medical history that may contain information or factors incorporated into the analysis of the functional images and/or volumes.

In the depicted embodiment, the image analysis system 10 also includes a structural image scanner 30 and associated structural image acquisition circuitry 32. The structural image scanner 30 is an imaging modality configured to acquire image data useful in generating structural, i.e., anatomic, images of the patient 14. Examples of such structural imaging modalities include CT, tomosynthesis, and other X-ray based imaging techniques, magnetic resonance imaging (MM) and ultrasound. As with the functional image scanner 12 described above, the structural image scanner 30 includes the data acquisition components of the structural imaging modality. Similarly, the structural image acquisition circuitry 32 is configured to acquire signals from the structural image scanner 30 and to provide any conversion (such as analog to digital conversion) or processing (such as image normalization, gain correction, artifact correction, and so forth) typically performed to facilitate the generation of suitable structural images. As discussed above with regard to the functional imaging components of the depicted image analysis system 10, the acquired structural image data is provided to image processing circuitry 18, which generates structural images and/or volumes. The structural images and/or volumes are in turn provided to image display circuitry 20 for display or printing and/or to the analysis circuitry 26 for analysis, as described above.

Figure 2:
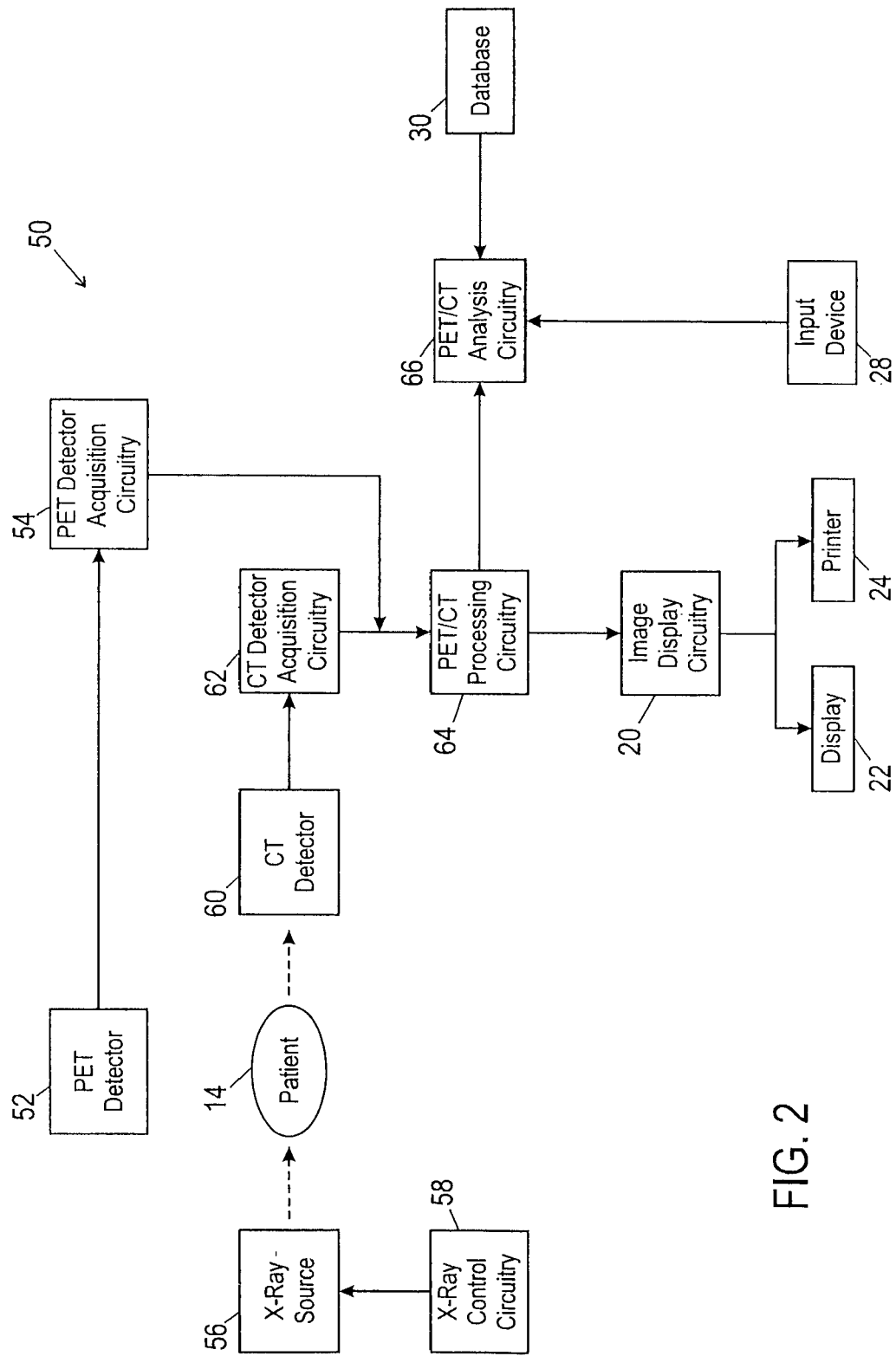
FIG. 2 is a diagrammatical view of an exemplary PET/CT imaging system for use in accordance with one embodiment of the present technique.

Referring now to FIG. 2, an exemplary PET/CT image analysis system 50 is depicted as a specific example of the image analysis system 10 of FIG. 1. The exemplary PET/CT image analysis system 50 includes CT scanning components, including an X-ray source 56 configured to emit X-rays through an imaging volume containing the patient 14 and X-ray control circuitry 58 configured to control the operation of the X-ray source 56 via timing and control signals. In addition, the included CT scanning components include a CT detector 60 configured to detect X-rays emitted by the source 56 after attenuation by the patient 14. As will be appreciated by those of ordinary skill in the art, the source 56 and CT detector 60 may be structurally associated in a number of ways. For example, the source 56 and CT detector 60 may both be mounted on a rotatable gantry, as in third-generation CT systems. Alternatively, one or both of the source 56 and detector 60 may be formed as mechanically stationary structures, as in fourth and fifth-generation CT systems.

In the depicted system, signals are acquired from the CT detector 60 by the CT detector acquisition circuitry 62. The CT detector acquisition circuitry 62, as noted with regard to the structural image acquisition circuitry 32 of FIG. 1, is configured to provide any conversion (such as analog to digital conversion) or processing (such as image normalization, gain correction, artifact correction, and so forth) typically performed to facilitate the generation of suitable CT images. Furthermore, the CT detector acquisition circuitry 62 may be configured to acquire diagnostic quality CT images, such as by utilizing prospective or retrospective gating techniques that compensate for respiratory motion or by otherwise acquiring CT image data during periods of respiratory stillness, such as during a breath hold. In such embodiments, higher quality CT images are acquired than in embodiments in which the patient 14 breathes and no compensation or correction is made for the respiratory motion. Furthermore, in embodiments where respiratory motion is accounted for or not allowed, the higher quality CT images may be more useful in providing anatomic localization and/or attenuation correction of the PET signals (discussed below).

The exemplary PET/CT image analysis system 50 also includes PET scanning components, including a PET detector 52. As will be appreciated by those of ordinary skill in the arts, the PET detector 52 may include a scintillator and associated optical sensing elements as well as timing circuits configured to differentiate coincident gamma ray pairs from spurious signals. In addition, the exemplary PET/CT image analysis system 50 includes PET detector acquisition circuitry 54 configured to acquire signals from the PET detector 52. The PET detector acquisition circuitry 54, as noted with regard to the functional image acquisition circuitry 16 of FIG. 1, is configured to provide any conversion or processing typically performed to facilitate the generation of suitable PET images.

In the depicted embodiment, the acquired PET and CT signals are provided to PET/CT image processing circuitry 64. For simplicity, the PET/CT image processing circuitry 64 is depicted as a single component though, as will be appreciated by those of ordinary skill in the arts, this circuitry may actually be implemented as discrete or distinct circuitries for each imaging modality. Conversely, the provided circuitry may be configured to process both the PET and the CT image signals and to generate respective PET and CT images and/or volumes therefrom. The generated PET and CT images and/or volumes may be provided to image display circuitry 20 for viewing on a display 22 or print out from a printer 24, as discussed above with regard to FIG. 1.

In addition, in the depicted embodiment, the PET and CT images are provided to PET/CT analysis circuitry 66. The PET/CT analysis circuitry 66 analyzes the PET and CT images and/or volumes in accordance with analysis routines, such as computer executable routines that may be run on general purpose or dedicated circuitry. In particular, the PET/CT analysis circuitry 66 is configured to identify and measure malignancy characteristics of a lesion that are visually or automatically identifiable in the respective PET and CT images or in the combined PET/CT image data. For example, the PET/CT analysis circuitry 66 may identify and/or measure malignancy characteristics such as vascular properties, calcification, and/or solidity with regard to a lesion observed in the CT image data. Likewise, the PET/CT analysis circuitry 66 may identify and/or measure malignancy characteristics such as the metabolism of glucose or other metabolites, anabolic activity, catabolic activity, and/or tissue necrosis with regard to a lesion observed in the PET image data.

Furthermore, the PET/CT analysis circuitry 66 may automatically detect the lesions for which malignancy characteristics are measured, such as by using threshold criteria or other techniques known in the art for segmenting regions of interest. Alternatively, a clinician or other viewer may manually detect the lesions or other regions of interest in either or both of the PET or CT images and/or volumes (such as in images viewed on the display 22). The clinician may then, via input device 28 (such as a keyboard and/or mouse), identify the lesions for analysis by the PET/CT analysis circuitry 66. In addition, to facilitate analysis either the PET/CT analysis circuitry 66 or image processing circuitry 64 may register the PET and CT images such that respective regions in each image correspond to one another or are aligned. In this manner, a region identified in an image of one modality may be properly identified in images generated by the other modality as well. For example, deformable registration routines (or other registration routines which account for patient motion) may be executed by the PET/CT image processing circuitry 64 or by the PET/CT analysis circuitry 66 to properly rotate, translate, and/or deform the respective images to achieve the desired correspondence of regions. Such deformable registration may be desirable where the PET and CT data is acquired serially or where the data acquisition period for one of the modalities, such as PET, is longer than for the other modality, such as CT. As will be appreciated by those of ordinary skill in the art, other registration techniques, such as rigid registration techniques, that achieve the desired degree of registration or correspondence can also be used in conjunction with the present technique.

While the input device 28 may be used to allow a clinician to identify regions of interest in the PET or CT images, the input device 28 may also be used to provide operator inputs to the PET/CT image analysis circuitry 66. These inputs may include configuration information or other inputs that may select the analysis routine to be executed or that may affect the operation of such an analysis routine, such as by specifying variables or factors taken into account by the analysis routines. Furthermore, inputs may be provided to the PET/CT image analysis circuitry 66 from a database 30 or other source of medical history that may contain information or factors incorporated into the analysis of the PET and CT images and/or volumes.

Figure 3:
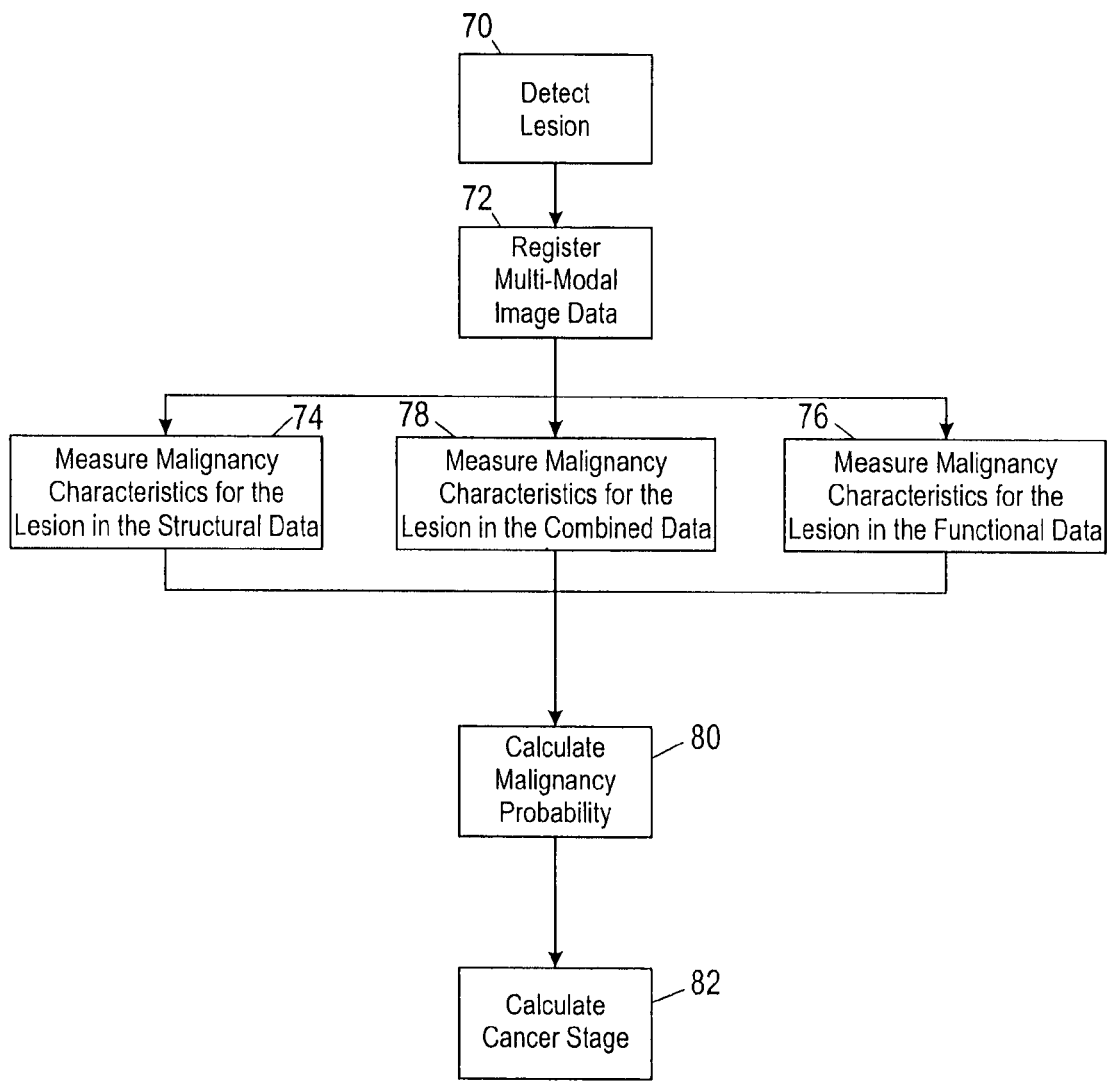
FIG. 3 is a flowchart depicting a technique for assessing lesion malignancy, in accordance with the present technique.

Turning now to FIG. 3, a flowchart is provided describing steps performed in the automated assessment of cancer, in accordance with the present technique, and as may be performed by the exemplary systems described in FIGS. 1 and 2. For illustrative purposes, the technique is discussed in the context of an analysis of a set of functional image data and a set of structural image data. As noted above, however, in other embodiments, more than one set of functional and/or structural image data may be employed in addition to or instead of the combination of functional and structural image data. As will be appreciated by those of ordinary skill in the art, however, the underlying principles of analysis are the same regardless of whether two or more sets of functional image data, two or more sets of structural image data, or a combination of structural and functional image data are employed.

As provided in the flowchart (and as noted above) a detection step 70 is provided in which one or more lesions are identified in structural and/or functional images of a patient or in the combined functional and structural images. In one embodiment, the detection step 70 is performed by automated detection routines, such as computer assisted detection routines, which identify lesions based on threshold or other segmentation/classification criteria from the surrounding image data. In an alternative embodiment, the detection step 70 is performed by a clinician or other viewer based on a visual review of one or both of the functional or structural images and/or volumes.

Based on the temporal and/or spatial variations in the underlying functional and structural image data, a registration step 72 may also be performed to register or align corresponding regions within the structural and functional images. Though the depicted embodiment suggests that the registration step 72 is performed subsequent to the detection step 70, in practice the registration step 72 may be performed before or after the detection step 70. In one embodiment, the registration step 72 utilizes an automated deformable registration technique that accounts for patient motion, such as after the acquisition of a set of CT image data but prior to the completion of the acquisition of a set of PET image data during an examination. In such an embodiment, the registration technique transforms reconstructed regions such that corresponding regions of interest in the structural and functional images are registered, i.e., aligned. As will be appreciated by those of ordinary skill in the art, a variety of registration techniques can be employed to suitably register concurrently or sequentially acquired functional and structural images.

Malignancy characteristics for the one or more detected lesions are automatically measured in the structural image data at step 74. For example, in one embodiment where the structural image data is CT image data, vascular properties, such as spiculation and angiogenesis, are measured by automated routines at step 74. Similarly, in this embodiment, malignancy characteristics such as calcification and solidity may be measured for a lesion automatically at step 74. As will be appreciated by those of ordinary skill in the art, the malignancy characteristics that are measured at step 74 will depend on the imaging modality employed and the malignancy characteristics that are typically evaluated in images generated by that modality.

Similarly, at step 76, malignancy characteristics for the one or more detected lesions are automatically measured in the functional image data. For example, in an embodiment where the functional image data is PET data, glucose metabolism, DNA synthesis, tumor hypoxia, and/or tissue necrosis may be measured for an identified lesion. Similarly, in other functional imaging modalities, these and/or other types of metabolic activity, such as catabolic and/or anabolic activity, and metabolite concentrations may be measured, depending on what malignancy characteristics are typically ascertained from images obtained using the respective functional imaging modality and imaging agent.

Optionally, at step 78, malignancy characteristics for the one or more detected lesions are automatically measured in the combined structural and functional image data. In embodiments where such detection occurs within the combined data, characteristics or other factors which are not apparent in either the structural or functional data alone, but which are apparent (or more easily quantified) in the combined data, may be measured.

In the depicted embodiment, the malignancy characteristics measured at steps 74, 76, and/or 78 are used to automatically calculate the probability of malignancy at step 80. As will be appreciated by those of ordinary skill in the art, the routines employed to perform this calculation may vary. In one embodiment, the calculation will be based, in full or in part, upon a clinical model of disease presentation. In another embodiment, the calculation will be based, in full or in part, upon machine learning methods operating on databases of prior clinical data, i.e., data where the clinical outcomes are known. In a further embodiment, the calculation will be based, in full or in part, on prior clinical information, such as genetic and family history, clinical history, habits, and so forth. In practice, some or all of these techniques, as well as other suitable techniques, may be employed for automatically calculating the probability of malignancy for the lesion or lesions detected at step 70.

In addition, an optional step 82 of automatically calculating a cancer stage is provided in the depicted embodiment. In one embodiment, the optional calculation of cancer stage at step 82 is based upon the locations and malignancy probabilities calculated for each lesion. For example, in one embodiment, a probability is calculated for each of the stages of the particular cancer stage model employed (such as the tumor, node, metastases (TNM) model). In this manner, a probability is calculated for the patient for each of the possible cancer stages provided by the model employed.

As one of ordinary skill in the art will appreciate, the processes for measuring malignancy characteristics and calculating malignancy and cancer stage probabilities described herein may be provided as one or more routines executable by the analysis circuitry or by processor-based components of the image analysis system 10 described herein. The routines may be stored or accessed on one or more computer-readable media, such as magnetic or optical media, which may be local to the image analysis system 10 or may be remotely accessible via a network connection, such as via the Internet or a local area network. Furthermore, access to or operation of the routines may be provided to an operator as part of the normal operation of the image analysis system 10.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method for evaluating a region of interest, comprising:
executing one more stored routines that, when executed, assess one or more malignancy characteristics in a first image data set acquired using a first imaging modality;
executing one more stored routines that, when executed, assess one or more malignancy characteristics in a second image data set acquired using a second imaging modality different from the first imaging modality;
executing one more stored routines that, when executed, assess one or more malignancy characteristics in a combined image data set generated using the first image data set and the second image data set; and
executing one more stored routines that, when executed, evaluate a region of interest identified in one or more of the first image data set, the second image data set, or the combined image data set based on the one or more malignancy characteristics, wherein the automatic evaluation comprises calculating a probability that the region of interest is malignant.

2. The method of claim 1, wherein at least part of the first image data set is acquired using one or more contrast agents.

3. The method of claim 1, wherein the first image data set comprises a contrast-enhanced set of image data and a non-enhanced set of image data.

4. The method of claim 1, wherein at least one of the first or second image data sets includes data acquired using one or more contrast agents.

5. The method of claim 1, wherein the region of interest comprises one of a lesion, a calcification, an organ, or a tumor.

6. The method of claim 1, wherein the one or more malignancy characteristics comprise at least one of a vascular property, a degree of calcification, a solidity, a glucose metabolism, DNA synthesis, hypoxia, an anabolic activity, a catabolic activity, a degree of hypoxia, a presence of a molecular species, or a tissue necrosis.

7. The method of claim 1, wherein the respective first and second imaging modalities comprise a structural imaging modality and a functional imaging modality.

8. The method of claim 1, wherein the respective first and second imaging modalities comprise a first structural imaging modality and a second structural imaging modality.

9. The method of claim 1, wherein the respective first and second imaging modalities comprise a first functional imaging modality and a second functional imaging modality.

10. The method of claim 1, wherein automatically evaluating the region of interest utilizes one or more of a clinical model, a machine learning process, or a priori information.

11. The method of claim 1, further comprising:
acquiring the first and second image data sets at least partially concurrently.

12. The method of claim 1, further comprising:
calculating a correspondence between the region of interest in the first and second image data sets.

13. The method of claim 1, further comprising:
registering the first and second image data sets.

14. The method of claim 13, wherein registering the first and second image data sets utilizes a deformable registration technique.

15. The method of claim 13, wherein registering the first and second image data sets utilizes a rigid registration technique.

16. The method of claim 1, wherein the step of automatically evaluating comprises at least one of automatically determining at least one of a likely cancer stage, a risk profile, one or more suggested treatments, a differential diagnosis, or a progression assessment.

17. One or more non-transitory machine-readable media, comprising:
a routine that assesses one or more malignancy characteristics in a first image data set acquired using a first imaging modality;
a routine that assesses one or more malignancy characteristics in a second image data set acquired using a second imaging modality different from the first imaging modality;
a routine that assesses one or more malignancy characteristics in a combined image data set generated using the first image data set and the second image data set; and
a routine that evaluates a region of interest identified in one or more of the first image data set, the second image data set, or the combined image data set based on the one or more malignancy characteristics, wherein the automatic evaluation comprises calculating a probability that the region of interest is malignant.

18. The one or more machine-readable media of claim 17, wherein the respective first and second imaging modalities comprise a structural imaging modality and a functional imaging modality.

19. The one or more machine-readable media of claim 17, wherein the respective first and second imaging modalities comprise a first structural imaging modality and a second structural imaging modality.

20. The one or more machine-readable media of claim 17, wherein the respective first and second imaging modalities comprise a first functional imaging modality and a second functional imaging modality.

21. The one or more machine-readable media of claim 17, wherein the routine for automatically evaluating the region of interest utilizes one or more of a clinical model, a machine learning process, or a priori information.

22. The one or more machine-readable media of claim 17, further comprising a routine for acquiring the first and second image data sets at least partially concurrently.

23. The one or more machine-readable media of claim 17, further comprising a routine for calculating a correspondence between the region of interest in the first and second image data sets.

24. The one or more machine-readable media of claim 17, further comprising a routine for registering the first and second image data sets.

25. The one or more machine-readable media of claim 17, wherein the routine for automatically evaluating determines at least one of a likely cancer stage, a risk profile, one or more suggested treatments, a differential diagnosis, or a progression assessment.

26. An analysis system, comprising:
analysis circuitry configured to assess one or more malignancy characteristics in a first image data set acquired using a first imaging modality, to assess one or more malignancy characteristics in a second image data set acquired using a second imaging modality different from the first imaging modality, to assess one or more malignancy characteristics in a combined image data set generated using the first image data set and the second image data set, and to evaluate a region of interest identified in one or more of the first image data set, the second image data set, or the combined image data set based on the one or more malignancy characteristics, wherein the automatic evaluation comprises calculating a probability that the region of interest is malignant.

27. The analysis system of claim 26, wherein at least one of the first or second image data sets comprise a set of functional image data.

28. The analysis system of claim 27, wherein the set of functional image data comprises one of a set of positron emission tomography (PET) image data, a set of single-photon emission computed tomography (SPECT) image data, a set of fluorescence imaging data or a set of functional magnetic resonance imaging (MRI) image data.

29. The analysis system of claim 26, wherein at least one of the first or second image data sets comprise a set of structural image data.

30. The analysis system of claim 29, wherein the set of structural image data comprises one of a set of computed tomography (CT) image data, a set of tomosynthesis image data, a set of ultrasound image data, or a set of magnetic resonance imaging (MRI) image data.

* * * * *

UNITED STATES PATENT AND TRADEMARK OFFICE
CERTIFICATE OF CORRECTION

| | | |
|---|---|---|
| PATENT NO. | : 8,010,184 B2 | Page 1 of 1 |
| APPLICATION NO. | : 11/291830 | |
| DATED | : August 30, 2011 | |
| INVENTOR(S) | : Avila et al. | |

It is certified that error appears in the above-identified patent and that said Letters Patent is hereby corrected as shown below:

In Column 4, Line 21, delete "(MM)" and insert -- (MRI) --, therefor.

Signed and Sealed this
Twenty-ninth Day of May, 2012

David J. Kappos
*Director of the United States Patent and Trademark Office*